(12) United States Patent
Joshi et al.

(10) Patent No.: US 6,171,581 B1
(45) Date of Patent: Jan. 9, 2001

(54) WATER AND OIL EMULSION SOLID ANTIPERSPIRANT/DEODORANT COMPOSITIONS

(75) Inventors: Vijay Kumar Joshi, Livingston; Charles George Shalotsky, Chatham; Tian Xiang Wang, Edison, all of NJ (US)

(73) Assignee: Revlon Consumer Products Corporation, New York, NY (US)

( * ) Notice: Under 35 U.S.C. 154(b), the term of this patent shall be extended for 0 days.

(21) Appl. No.: 09/314,216

(22) Filed: May 19, 1999

Related U.S. Application Data

(63) Continuation-in-part of application No. 09/216,199, filed on Dec. 18, 1998, now abandoned.

(51) Int. Cl.[7] .................. A61K 7/32; A61K 7/00
(52) U.S. Cl. ................. 424/65; 424/400; 424/401; 424/DIG. 5; 514/937; 514/944
(58) Field of Search .................... 424/400, 401, 424/65, DIG. 5; 514/932, 944

(56) References Cited

U.S. PATENT DOCUMENTS

| | | | |
|---|---|---|---|
| 4,265,878 * | 5/1981 | Keil | 424/68 |
| 4,822,602 * | 4/1989 | Sabatelli | 424/65 |
| 5,266,321 * | 11/1993 | Shukuzaki et al. | 424/401 |
| 5,412,004 | 5/1995 | Tachibana | 524/27 |
| 5,597,849 * | 1/1997 | McGinity et al. | 514/648 |
| 5,599,533 | 2/1997 | Stepniewski | 424/78.02 |
| 5,654,362 | 8/1997 | Schulz | 524/862 |
| 5,833,965 * | 11/1998 | Sun et al. | 424/66 |
| 5,849,314 | 12/1998 | Dobkowski | 424/401 |
| 5,922,309 * | 7/1999 | Brewster | 424/65 |
| 5,942,215 * | 8/1999 | Edwards et al. | 424/65 |
| 5,998,542 * | 12/1999 | Horne et al. | 524/731 |
| 6,010,687 * | 11/1998 | Cox et al. | 424/65 |

FOREIGN PATENT DOCUMENTS

| | | |
|---|---|---|
| 95/31967 * | 11/1995 | (WO) . |
| WO97/44010 | 11/1997 | (WO) . |
| WO98/00097 | 1/1998 | (WO) . |
| WO98/18438 | 5/1998 | (WO) . |
| WO98/42307 | 10/1998 | (WO) . |

* cited by examiner

Primary Examiner—Shelley A. Dodson
Assistant Examiner—Marina Lamm
(74) Attorney, Agent, or Firm—Julie Blackburn

(57) ABSTRACT

A water and oil emulsion solid antiperspirant or deodorant composition comprising, by weight of the total composition:
- 0.1–30% of a silicone elastomer,
- 0.05–30% of a gellant,
- 1–25% of an antiperspirant or deodorant active,
- 1–90% water, and
- 1–75% oil.

20 Claims, No Drawings

WATER AND OIL EMULSION SOLID ANTIPERSPIRANT/DEODORANT COMPOSITIONS

RELATED APPLICATIONS

This application is a continuation-in-part of U.S. patent application Ser. No. 09/216,199, filed Dec. 18, 1998 now abondoned.

TECHNICAL FIELD

The invention is in the field of antiperspirant/deodorant compositions.

SUMMARY OF THE INVENTION

Antiperspirants and deodorants are sold in various forms such as gels, solids, roll-ons, and aerosols. Solids are very popular with consumers. However, typical solids are anhydrous and have certain drawbacks such as tackiness, greasiness, or inadequate payoff. Solids which contain substantial levels of water are desireable because the presence of water ameliorates some of the drawbacks. However, water based solids may sometimes be unstable. In addition, if the gelling agents used to form the water based gel form a gel structure that is too "tight", the sticks will not have the appropriate payoff.

The object of the invention is to prepare a water and oil emulsion solid antiperspirant/deodorant composition with commercially acceptable payoff.

The object of the invention is to prepare a water and oil emulsion solid antiperspirant/deodorant composition containing silicone elastomers.

SUMMARY OF THE INVENTION

A water and oil emulsion solid antiperspirant composition comprising, by weight of the total composition:
- 0.1–30% of a silicone elastomer,
- 0.05–30% of a gellant,
- 1–25% of an antiperspirant active,
- 1–90% water, and
- 1–75% oil.

A water and oil emulsion solid deodorant composition comprising, by weight of the total composition:
- 0.1–30% of a silicone elastomer,
- 0.05–30% of a gellant,
- 1–20% of a deodorant active,
- 1–90% water, and
- 1–75% oil.

DETAILED DESCRIPTION

The emulsion compositions of the invention are solid at room temperature. The emulsions may be water-in-oil or oil-in-water. The term "solid" means that the compositions may be in the form of solid sticks or the soft solid form (which is a solid but compressible viscous gel). The emulsion compositions contain the following ingredients.

SILICONE ELASTOMER

The emulsion compositions of the invention contain 0.1–30%, preferably 0.1–20%, more preferably 0.5–15% of a silicone elastomer. Suitable silicone elastomers for use in the compositions are as set forth in U.S. Pat. Nos. 5,266,321; 4,980,167; 4,742,142; 5,599,533; and 5,412,004; all of which are incorporated by reference in the entirety. The silicone elastomers may be emulsifying or nonemulsifying. The term "emulsifying" means that the silicone elastomer contains polar functional groups that provide emulsification properties. The term "nonemulsifying" means that the silicone elastomer does not contain polar functional groups that provide emulsifying properties. The silicone elastomers are generally three dimensional cross-linked chain polymers which have rubber-like properties.

One type of nonemulsifying silicone elastomer that may be used in the compositions of the invention are those formed by the reaction of hydrogen substituted siloxanes and an alpha, omega diene, in the presence of a platinum catalyst, and a low molecular weight linear or cyclic siloxane. The hydrogen substituted siloxane have the general formulas:

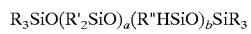

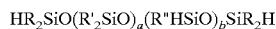

wherein R, R', and R" are each independently alkyl groups having 1–22 carbon atoms, a is 0–250, b is 1–250, and c is 0–250. Any one or more of the above mentioned substituted siloxanes may be used in the reaction. The alpha omega dienes used in the reaction have the general formula:

wherein x is 1–20. Examples of such alpha omega dienes are 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene. These silicone elastomers are disclosed in U.S. Pat. No. 5,654,362, which is hereby incorporated by reference in its entirety.

Other nonemulsifying silicone elastomers suitable for use in the invention are disclosed in U.S. Pat. No. 5,599,533, which is hereby incorporated by reference. These silicone elastomers are three dimensional cross-linked polymers formed by reaction of a methyl hydrogen siloxane and an organopolysiloxane having unsaturated groups such as vinyl or allyl, preferably in the presence of a platinum catalyst. In these silicone elastomers the cross-linking group is an organopolysiloxane, rather than an alpha omega diene, as above.

Other silicone elastomers for use in the compositions may be formed by the reaction of methyl hydrogen organosiloxanes with vinyl or allyl terminated organosiloxane that is substituted with other functional groups, for example, fatty alkyl groups or hydroxyl alkyl groups. For example, a suitable silicone elastomer may be formed by the reaction of a methyl hydrogen siloxane substituted with a $C_{16\text{-}22}$ alkyl group. Or, the vinyl or allyl terminated organosiloxane may be substituted with such a fatty alkyl group.

Also suitable are emulsifying silicone elastomers disclosed in U.S. Pat. No. 5,412,004. These elastomers are formed by the addition polymerization of I. an organohydrogenpolysiloxane having the following formula:

(A) 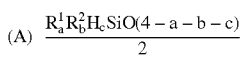

(1) $R^1$ is a substituted or unsubstituted alkyl, aryl, or aralkyl group having 1–18 carbon atoms, or a halogenated hydrocarbon group; and (2) $R^2$ is —$C_nH_{2n}O(C_2H_4O)_d(C_3H_6O)_eR_3$
  (a) wherein $R^3$ is a hydrogen, a saturated aliphatic hydrocarbon group having 1–10 carbon atoms, or a group —(CO)—$R^5$
    (i) wherein $R^5$ is a saturated aliphatic hydrocarbon having 1 to 5 carbon atoms,
  (b) d is an integer of 2 to 200,
  (c) e is an integer of 0 to 200, provided that d+e is 3–200; and
  (d) n is 2 to 6;
(3) a is 1 to 2.5;
(4) b is 0.001 to 1.0; and
(5) c is 0.001 to 1.0; or an organohydrogenpolysiloxane having the following formula
(B) or on organohydrogenpolysiloxane having the following formula:

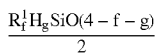

(1) wherein $R^1$ is the same as defined in formula I(A) above,
(2) f is 1.0 to 3.0;
(3) g is 0.001 to 1.5;
(C) or a mixture of said organohydrogenpolysiloxanes of formulas I(A) and I(B); and
II. a polyoxyalkylene having the following formula:
(A) $C_mH_{2m-1}O(C_2H_4O)_h(C_3H_6O)_iC_mH_{2m-1}$
(1) wherein h is an integer of 2 to 200,
(2) i is an integer of 0 to 200 provided that h+i is 3 to 200; and
(3) m is 2 to 6;
(B) or an organopolysiloxane having the following formula

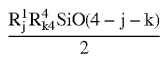

(1) wherein $R^1$ is the same as defined in formula I(A) above,
(2) $R^4$ is a monovalent hydrocarbon group having an aliphatic unsaturated bond at the terminal thereof and containing 2 to 10 carbon atoms;
(3) j is 1.023 to 3.0; and
(4) k is 0.001 to 1.5;
(C) or a mixture of the polyoxyalkylene of II(A) and the organopolysiloxane of II(B), wherein at least one organohydrogenpolysiloxane of formulas I or at least one polyoxyalkylene of formulas II is contained as an essential component of the addition polymerization.

Preferred silicone elastomers are formed by the reaction of an organohydrogenpolysiloxane having the formula:

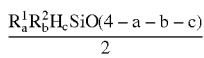

wherein $R^1$ is a $C_{1-18}$ alkyl, and $R^2$ is H; with a polyoxyalkylene having the formula:

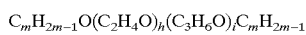

wherein m, h, and I are as defined above. Particularly preferred is an emulsifying silicone elastomer sold by Shin-Etsu Silicones under the tradename KSG 21.

Also preferred are silicone elastomers formed by reaction of a methyl hydrogen siloxane and an organopolysiloxane having unsaturated groups such as vinyl or allyl, preferably in the presence of a platinum catalyst.

In general, silicone elastomers suitable for use in the invention may be purchased from Grant Industries under the tradename Gransil (SR-CYC, SR, DMF 10, SR-DC556), from Shin-Etsu under the tradenames KSG15, KSG17, KSG16, KSG18, KSG21 Dow Corning under the tradenames Trefil E-505C, Trefil E-506C, of 9506; and General Electric under the tradenames SFE 168. Examples of these elastomers include those having the CTFA names dimethicone/vinyl dimethicone crosspolymer, cetearyl dimethicone/vinyl dimethicone crosspolymer, and the like.

GELLANT

The composition of the invention comprises 0.05 to 30%, preferably 0.1–20%, more preferably 0.5–15% of a gellant. Suitable gellants are carboxylated salt gelling agents, dibenzylidene alditols, polysaccharides, polysaccharide/protein complexes, and the like.

I. Carboxylated Salt Gelling Agents

The term "carboxylated salt gelling agent" means a gelling agent that is formed by the reaction of a salt with a compound containing at least one carboxylic acid group. Preferably the carboxylic acid-containing compound is a fatty acid and the carboxylated salt gelling agent is the salt of a water insoluble fatty acid and a base. While the fatty acid used to make the carboxylated salt gelling agent is generally water insoluble, the resulting gelling agent may be water soluble or water insoluble. Preferably, the carboxylated salt gelling agent in accordance with this invention is water soluble, i.e. after the water insoluble fatty acid is reacted with the metallic cation (such as sodium) the gelling agent is water soluble or dispersible Suitable fatty acids used to make the gelling agent are $C_{12-40}$ straight or branched chain, saturated or unsaturated fatty acids. Suitable fatty acids include lauric, myristic, palmitic, stearic, oleic, linoleic, linolenic, behenic, caprylic, stearic, and so on. In addition, oils containing fatty acid mixtures, such as palm kernel, olive, tallow, peanut, rapeseed, and the like may be used as the fatty acid component. Preferred are $C_{16-22}$ fatty acids such as lauric, stearic, or behenic. Most preferred is where the fatty acid is stearic acid.

A variety of cations may be used. Generally the type of cation selected will determine whether the resulting gelling agent is water soluble or water insoluble. Generally cations such as sodium, potassium, or low molecular weight amines or alkanolamines will provide water soluble gelling agents. Suitable amines are ammonia and derivatives thereof. Suitable alkanolamines include mono- di- and triethanolamines.

Examples of gelling agents which may be used in the compositions of the invention are sodium, potassium, aluminum, magnesium, or calcium salts of stearic, behenic, caprylic, tallowic, tallic, cocoic, or lauric acids, and so on. Preferably the gelling agent used in the compositions of the invention are water soluble salts of fatty acids and sodium, and in particular sodium stearate.

II. Dibenzylidene Alditols

Also suitable as the gellant are a class of compounds referred to as dibenzylidene alditols, for example dibenzylidene sorbital monoacetal. Examples of dibenzylidene alditols include dibenzyl monosorbitol acetals disclosed in U.S. Pat. No. 4,518,582, which is hereby incorporated by reference.

III. Polysaccharides

Polysaccharide gellants are also suitable for use in the compositions of the invention. The term "polysaccharide gellant" means a water soluble compound or composition (i) containing at least one saccharide moiety; and (ii) which, upon mixing with water in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm$^2$ at 25° C. as measured using a TA.XT2i texture analyzer with a ½ inch diameter cylindrical probe. The term "saccharide moiety" means a polyhydroxy aldehyde or ketone, or acid hydrolysis product thereof, which, preferably, has the general formula $C_x(H_2O)_y$. Examples of saccharide moieties include the D and L forms of glucose, fructose, xylose, arabinose, ficose, galactose, pyruvic acid, succinic acid, acetic acid, galactose, 3,6-anhydro-galactose sulfate, galactose-4-sulfate, galactose-2-sulfate, galactose-2,6-disulfate, mannose, glucuronic acid, mannuronic acid, guluronic acid, galactouronic acid, rhamnose, and so on. Preferably the polysaccharide gellants have a molecular weight ranging from about 500 to 15,000,000 daltons, preferably 5,000 to 1,000,000, more preferably 25,000 to 500,000 daltons. Polysaccharide gellants which fulfill the above criteria include polysaccharides such as galactans, galactomannans, glucomannans, polyuronic acids, and the like. Suitable galactans are agar, agarose, and kappa carageenan, iota carageenan, lambda carageenan. Examples of suitable galactomannans are locust bean gum and guar; examples of glucans are cellulose and derivatives thereof, starch and derivatives, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on.

Preferred are galactans, in particular agarose, which is a polysaccharide comprised of basic repeating units of 1,3-linked beta-D-galactopyranose and 1,4-linked 3,6-anhydro-alpha-L-galactopyranose saccharide moieties. The agarose may be substituted by hydrophobic or hydrophilic groups. Examples of hydrophobic groups are alkoxy, in particular, methoxy. Examples of hydrophilic or polar groups are sulfate, pyruvate and the like. Examples of such substitutions are taught in Aoki, T.T.; Araki & M. Kitamikado; 1990, Vibrio sp. AP-2. *Eur. J. Biochem*, 187, 461–465, which is hereby incorporated by reference. The average molecular weight of agarose ranges between 35,700 and 144,000 daltons. The agarose suitable for use in the compositions of the invention may be from any suitable source or locate. For example an article authored by M. Lahaye and C. Rochas, *Hydrobiologia*, 221, 137–148, 1991, which is hereby incorporated by reference, discusses the numerous different types of agarose from different origins of seaweed species, all of which are suitable for use in the compositions of the invention. Also suitable for use in the compositions of the invention are chemically modified agaroses, such as those taught in an article authored by K. B. Guiseley in *Industrial Polysaccharides:Genetic Engineering, Structure/Property Relations and Applications*, Edited by M. Yalpani, 1987, Elsevier Science Publishers, which is hereby incorporated by reference. The Guiseley article teaches methods for the chemical modification of agaroses to obtain optimum gelling properties. One example of modified agarose is a hydroethylated agarose which is sold under the brand names Sea-Plaque and SeaPrep. In general, any modification of agarose which does not affect the helical conformation (i.e. which is obtained via linkage of the 06 and 04 of galactose to the 02 of 3,6-anhydrogalactose) will preserve the gelling capability.

In the most preferred embodiment of the invention, the polysaccharide gellant is agarose, which can be purchased from Seakem under the tradename Seakem LG agarose.

IV. Protein/Polysaccharide Complexes

Another suitable gellant may be protein/polysaccharide complexes ("PPC"). Such PPC's are formed by the reaction of a protein and an anionic polysaccharide containing a sufficient number of pendant hydrophilic groups such that the polysaccharide has a net positive or negative charge density, preferably a net negative charge density. The net charge of the PPC will depend upon the ratio of protein to polysaccharide in the PPC and the pH at which the PPC is made. For example, if the PPC is made at a pH which is above the isoelectric point of the protein, it will have a negative charge regardless of the ratio of protein to polysaccharide. On the other hand, if it is made at a pH which is below the isoelectric point of the protein, the pH of the PPC may be positively charged if the total positive charge from the protein is more than the negative charge polysaccharide and protein combined. The protein used must contain a sufficient number of amino and/or carboxyl groups such that it is capable of reacting with the hydrophilic groups on the anionic polysaccharide to form a PPC. Preferably the pendant hydrophilic groups of the polysaccharide react with amino and/or carboxyl groups of the protein via formation of ionic bonds or electrostatic interaction. A variety of proteins may be used to form the PPC. The term "protein" when used in accordance with this invention means a peptide chain having at least two amino acid residues, preferably at least five, and more preferably more than one hundred amino acid residues. Most preferably the protein is a high molecular weight polypeptide which is preferably water soluble, and may be natural, plant (vegetable) proteins, or animal derived proteins, as well as synthetic proteins provided they react with the hydrophilic pendant groups on the polysaccharide to form a PPC. The isoelectric point of the protein used to make the PPC is not critical. Examples of natural proteins include albumen, amylase, amyloglucosidase, arginine/lysine polypeptide, casein, catalase, collagen, crystalline, cytochrome C, deoxyribonuclease, elastin, fibronectin, gelatin, gliadin, glucose oxidase, glycoproteins, hexyldecyl ester of hydrolyzed collagen, human placental protein, human placental enzymes, iodized corn protein, keratin, lactoferrin, lactoglobulin, lactoperoxidase, lipase, milk protein, hyristoyl glycine/histidine/lysin polypeptide, nisin, oxido reductase, pancreatin, papin, pepsin, placental protein, protease, saccharomyces polypeptides, serum albumin, serum protein, silk, sodium stearoyl lactalbumin, soluble proteoglycan, soybean palmitate, soy, egg, peanut, cottonseed, sunflower, pea, whey, fish, seafood, subtilisin, superoxide dismutase, sutilains, sweet almond protein, urease, wheat germ protein, wheat protein, whey protein, zein, hydrolyzed vegetable protein, and the like. Preferred is casein which is a mixture of phosphoproteins obtained from cow's milk; and milk protein which is a mixture of proteins obtained from cow's milk.

Synthetic proteins or polypeptides may also be suitable. Synthetic proteins may be made by solid phase synthesis, or via recombinant biotechnology processes.

A variety of anionic polysaccharides are suitable for use in making the PPC used in the compositions of the invention, provided the anionic polysaccharide contains a sufficient number of pendant hydrophilic groups to cause the resulting PPC to exhibit a net positive or negative charge. In addition, the anionic polysaccharide must be capable of reacting with the protein to form a PPC having a protein/polysaccharide ratio of about 100 to 1: to 1: 100. Suitable pendant hydrophilic groups include groups, i.e. a group containing the moiety —$SO_3^-$; —$SO_4^-$; or —$OSO_2O$—; phosphate, pyruvate, and the like. The term "polysaccharide" when used in accordance with the invention means a water soluble anionic polysaccharide which (i) contains at least five saccharide moieties; and (ii) which, upon mixing with water in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm² at 25° C. as measured using a TA.XT2i texture analyzer with a ½ inch diameter cylindrical probe. The term "saccharide moiety" means a polyhydroxy aldehyde or ketone, or acid hydrolysis product thereof, which, preferably, has the general formula $C_x(H_2O)_y$. Examples of saccharide moieties include the D and L forms of glucose, fructose, xylose, arabinose, fucose, galactose, pyruvic acid, succinic acid, acetic acid, galactose, 3,6-anhydro-galactose sulfate, galactose-4-sulfate, galactose-2-sulfate, galactose-2,6-disulfate, mannose, glucuronic acid, mannuronic acid, guluronic acid, galactouronic acid, rhamnose, and so on. Preferably the anionic polysaccharides used to make the PPC have molecular weights ranging from about 500 to 15,000,000 daltons, preferably 5,000 to 1,000,000, more preferably 25,000 to 500,000 daltons.

Examples of suitable anionic polysaccharides include galactans, galactomannans, glucomannans, polyuronic acids, and the like, which exhibit the requisite number of pendant hydrophilic groups, which are preferably sulfate. Suitable galactans are agar, agarose, kappa carageenan, iota carageenan, lambda carageenan, and the like. Examples of suitable galactomannans are locust bean gum and guar; examples of glucans are cellulose and derivatives thereof, starch and derivatives, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on. Also suitable are dextran sulfate, heparin, pectin, sodium alginate, and mixtures thereof Preferred are galactans, particularly galactans where the pendant hydrophilic groups are sulfate groups. Most preferred is agar and carageenan, which are anionic polysaccharides comprised of basic repeating units of 1,3-linked beta-D-galactopyranose and 1,4-linked 3,6-anhydro-alpha-L-galactopyranose saccharide moieties and having pendant sulfate groups. These galactans may be further modified as taught in Aoki, T. T.; Araki & M. Kitamikado; 1990, Vibrio sp. AP-2. *Eur. J. Biochem*, 187, 461–465, which is hereby incorporated by reference, provided it contains the requisite number of hydrophilic pendant groups. The average molecular weight of agar ranges between 35,700 and 144,000 daltons. The galactans suitable for use in the compositions of the invention may be from any suitable source or locale. For example an article authored by M. Lahaye and C. Rochas, *Hydrobiologia*, 221, 137–148, 1991, which is hereby incorporated by reference, discusses the numerous different types of galactans from different origins of seaweed species, all of which are suitable for use in the compositions of the invention. Also suitable for use in the compositions of the invention are chemically modified galactans, such as those taught in an article authored by K. B. Guiseley in *Industrial Polysaccharides:Genetic Engineering, Structure/Property Relations and Applications*, Edited by M. Yalpani, 1987, Elsevier Science Publishers, which is hereby incorporated by reference. The Guiseley article teaches methods for the chemical modification of agar to obtain optimum gelling properties. In general, any modification of the galactans which does not affect the helical conformation (i.e. which is obtained via linkage of the O6 and O4 of galactose to the O2 of 3,6-anhydrogalactose) will preserve the gelling capability and is suitable for use in the compositions of the invention provided the requisite number of hydrophilic groups are present. The hydrophilic groups provide a polysaccharide which is water soluble.

Generally, the amino and/or hydroxyl or carboxyl groups found on the protein will react with the pendant hydrophilic groups on the anionic polysaccharide to form a complex, either alone or in the presence of metal ions such as calcium, sodium, magnesium, iron, potassium, and the like, depending on the pH at which the complexation reaction is conducted. For example, if the complexation reaction is conducted above the isoelectric point of the protein used to make the PPC, it is preferable to use a metal ion to facilitate the complexation reaction. On the other hand, if the reaction is conducted at a pH which is at the isoelectric point of the protein used to make the PPC, a metal ion may be desired to facilitate complexation, but is not necessary. Typical reactions are as set forth below:

Complexation Reaction Conducted at pH Above the Isoelectric Point of the Protein

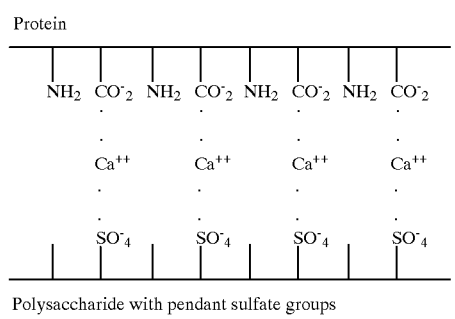

With a typical reaction being:

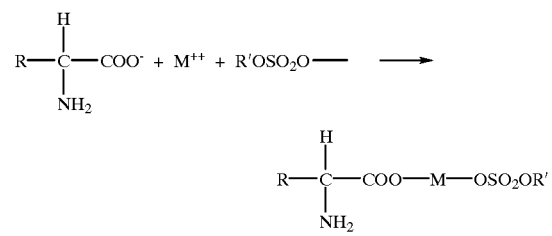

Complexation reaction conducted a pH near the isoelectric point of protein

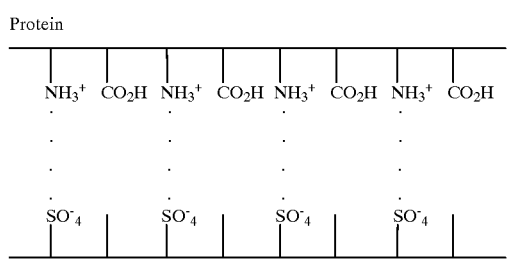

With typical reactions being:

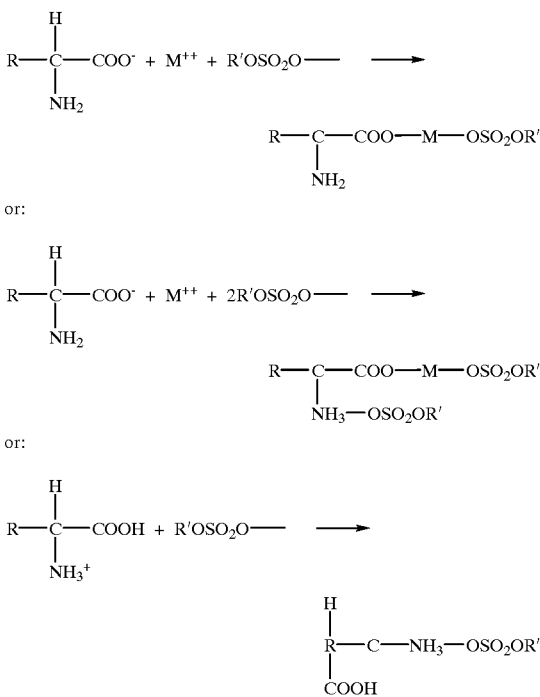

Preferably, the ratio of protein to polysaccharide in the PPC is 1:100 to 100:1, more preferably 1:50 to 50:1, most preferably 1:25 to 25:1. Preferably the PPC must contain a net negative charge. For example, when the protein having a net positive charge is reacted with the anionic polysaccharide having a net negative charge, the net negative charge of the polysaccharide is greater than the net positive charge of the protein, thus resulting in a PPC which has a net negative charge. A negative or positive charge will ensure that the PPC is water soluble, or at the very least optimally dispersible in water.

The PPC is made by combining appropriate amounts of the protein and polysaccharide in water at temperatures ranging from 25 to 90° C. Some PPC's may form at room temperature depending on the protein and polysaccharide chosen to make the PPC. Suitable ratios are 100 to 1 parts of protein to 1 to 100 parts polysaccharide. Preferably, the protein/polysaccharide complexation reaction should be conducted at a pH which is greater than the isoelectric point of the protein used to make the PPC. If more than one protein is used to make the PPC, it is recommended that the pH be equal to or greater than one or more of the proteins used. Generally, when the complexation reaction is conducted at a pH which is below the isoelectric point of the protein, it is not necessary to add metal ions. However, at this pH, the PPC may form a water insoluble precipitate (also referred to as an M-complex) if the ratio of protein to polysaccharide is not optimal. For example, the isoelectric point of casein is about 4.6. If the complexation reaction of casein with agar is conducted at pH 3.7, an M-complex (i.e. a water insoluble precipitate) is formed when the ratios of protein to polysaccharide are not optimized. Thus, it is preferred that the complexation reaction occur at a pH which is equal to or greater than the isoelectric point of the protein used to make the PPC. At this pH it may be desireable to add metal ions, such as calcium, potassium, sodium, magnesium, and the like, which will facilitate the complexation reaction. When the complexation reaction is conducted at a pH which is equal to or greater than the isoelectric point of the protein, a T-complex (also known as a water soluble or water dispersible complex) results. While optimally, a T-complex is formed at a pH which is equal to or greater than the isoelectric point of the protein used to form the PPC, after it is formed it is stable and may be incorporated into cosmetic compositions which have a pH which is substantially below the isoelectric point of the protein.

V. Other Gellants

A variety of other gellants may be used as well, such as fatty alcohols having the formula R—OH wherein R is a straight or branched chain $C_{6-30}$ alkyl, preferably a $C_{12-22}$ alkyl. Examples of fatty alcohols include cetyl alcohol, stearyl alcohol, behenyl alcohol, and the like.

Also suitable are various fatty acids having the general formula R—COOH wherein R is a straight or branched chain alkyl which may be unsubstituted, or substituted with one or more hydroxyl groups. Examples of these acids include stearic acid, 12-hydroxystearic acid, and the like. Also useful are esters and amides of fatty acids, such as 12-hydroxystearic acid. Examples of these gellants include 12-hydroxystearic acid methyl ester, 12-hydroxystearic acid cyclohexyl amide, 12-hydroxystearic acid t-butyl amide, and the like.

N-acyl amino acid amides, n-acyl amino acid esters prepared from glutamic acid, lysine, glutamine, aspartic acid, and combinations thereof, as also possible gellants. Examples of these gellants are set forth in U.S. Pat. No. 5,429,816, which is hereby incorporated by reference.

Preferably, the gellant used in the composition of the invention is a polysaccharide, in particular, agarose.

ANTIPERSPIRANT ACTIVE

The compositions of the invention contain 1–30%, preferably 5–25%, more preferably 10–25% by weight of the total single phase aqueous composition of antiperspirant active salt.

The term "antiperspirant active salt" or "antiperspirant salt" means any compound or composition having antiperspirant activity, preferably astringent metallic salts such as the inorganic and organic salts of aluminum, zirconium, and zinc, and mixtures thereof Particularly preferred are the aluminum and zirconium salts such as aluminum halides, aluminum hydroxide halides, zirconyl oxide halides, zirconyl hydroxy halides, and mixtures thereof. Aluminum salts include those of the formula:

$$Al_2(OH)_aCl_b \cdot xH_2O$$

wherein a is from about 2 to 5; a+b=6; x is from about 1 to about 6; and wherein a, b, and x may have non-integer values. Zirconium salts include those of the formula:

$$ZrO(OH)_{2-a}Cl_a \cdot xH_2O$$

wherein a is from about 1.5 to about 1.87; x is from about 1 to about 7; and wherein a and n may have non-integer values.

Examples of aluminum and zirconium salts include aluminum chloride, aluminum chlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum zirconium octachlorohdrate, aluminum zirconium octachloroydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium trichlorohydrate, aluminum zirconium trichlorohydrex GLY, and mixtures thereof Particularly preferred zirconium salts are those complexes also containing aluminum and glycine, in particular, aluminum zirconium tetrachlorohydrex GLY. The antiperspirant salts used in the composition of the invention are solubilized in the water. While preferably the antiperspirant salts are completely dissolved in the water, in some cases small amounts of salts may not be dissolved, i.e. may remain in the crystalline or suspensoid form.

WATER

The single phase aqueous composition of the invention also contains water. Preferably the composition contains 1–90%, more preferably 3–80%, most preferably 5–60% water.

The invention also comprises a deodorant composition having the same ranges of ingredients as set forth for the antiperspirant composition. The deodorant active may be added to the composition in addition to the antiperspirant active salt, or deodorant composition may be made by removing the antiperspirant actives completely and substituting an effective amount of a deodorant active.

DEODORANT ACTIVE

A range of 0.1–30% of deodorant active is suggested in deodorant compositions. Examples of suitable deodorant actives include fragrances, ammonium phenolsulfonate, benzalkonium chloride, benzethonium chloride, bromochlorophene, cetylpyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenoisulfonate, triclocarbone, triclosan, zinc phenolsulfonate, zinc ricinoleate, and mixtures thereof The preferred deodorant active is triclosan, fragrance and the like.

OIL

The compositions of the invention contain 1–75%, preferably 5–65%, more preferably 10–50% of at least one oil. The oils used may be volatile or nonvolatile. Often silicone elastomers are purchased in the form of gels of the elastomer in a volatile or nonvolatile silicone. The oil present in the compositions of the invention may be found as part of the elastomer composition alone, the oil phase alone, or both.

The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. Suitable volatile solvents generally have a viscosity of 0.5 to 10 centistokes at 25° C. Suitable volatile oils include linear silicones, cyclic silicones, paraffinic hydrocarbons, or mixtures thereof Cyclic silicones (or cyclomethicones) are of the general formula:

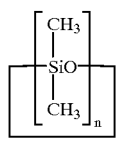

where n=3–7.

Linear volatile silicones in accordance with the invention have the general formula:

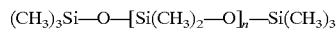

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the C.T.F.A. Cosmetic Ingredient Handbook, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof Also suitable as the nonvolatile oil are various fluorinated oils such as fluorinated silicones, fluorinated esters, or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

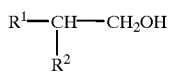

with a carboxylic acid having the general formula:

or

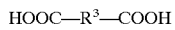

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formed by the reaction of a guerbet alcohol and carboxylic acid (as defined above), and a fluoroalcohol having the following general formula:

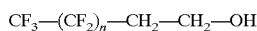

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Georgia as Developmental Ester L61125A, under the tradename Silube GME-F.

Preferably, the compositions of the invention contain a mixture of volatile and nonvolatile silicone oils, so that the amount of volatile oil is about 1–10%, by weight of the total composition, and the amount of nonvolatile oil is about 1–10% by weight of the total emulsion composition. In the preferred embodiment of the invention, the preferred volatile oil is cyclomethicone and the preferred nonvolatile oil is a low viscosity dimethicone. i.e dimethicone having a viscosity of about 5–25 centipoise at 25° C.

OTHER INGREDIENTS

The composition may contain a variety of other ingredients including humectants, surfactants, gel structure modifiers, preservatives, and the like.

I. Surfactants

Preferably the composition contains one or more surfactants, preferably nonionic surfactants which may be silicone surfactants or organic surfactants. Examples of silicone surfactants which may be used are set forth in U.S. Pat. No. 5,725,845, which is hereby incorporated by reference. Suitable organosiloxane emulsifiers generally contain at least one lipophilic radical or portion and at least one hydrophilic radical or portion. The organosiloxane used in the invention is preferably a liquid or semi-solid at 25° C. The polymeric organosiloxane is generally a water-in-oil or oil-in-water type surfactant which is preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB=7+11.7 \times \log M_w M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxypolypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof The $C_{1-40}$ alkyl may be non-interrupted, or interruped by one or more oxygen atoms, a benzene ring, amides, esters, or other functional groups.

The polymeric organosiloxane emulsifier used in the invention may have any of the following general formulas:

$$M_xQ_y,$$

or $$M_xT_y,$$

or $$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D'' are difunctional siloxy units substituted with methyl, hydrogen, a lipophilic radical, a hydrophilic radical or mixtures thereof In this general formula:

x=0–5000, preferably 1–1000
y=0–5000, preferably 1–1000, and
z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference.

Particularly preferred is a linear silicone of the formula:

$$MD_xD'_yD''_zM$$

wherein $M=RRRSiO_{1/2}$
D and $D'=RR'SiO_{2/2}$
$D''=RRSiO_{2/2}$
x, y, and z are each independently 0–1000,
where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D=Si[(CH_3)][(CH_2)_nCH_3]O_{2/2}$ where n=1–40, $D'=Si[(CH_3)][(CH_2)_o—O—PE)]O_{2/2}$ where PE is $(—C_2H_4O)_a(—C_3H_6O)_bH$, o=0–40, a=1–100 and b=1–100, and $D''=Si (CH_3)_2O_{2/2}$ Typical examples of preferred organosiloxane emulsifiers in accordance with the invention include those set forth below:

I.

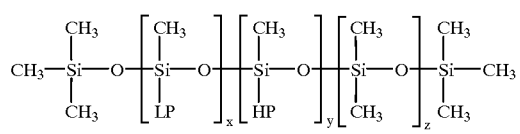

II.

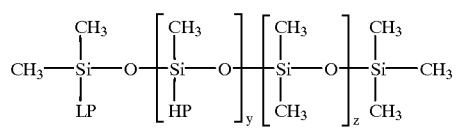

III.

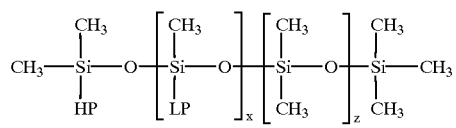

IV.

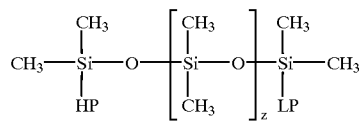

V.

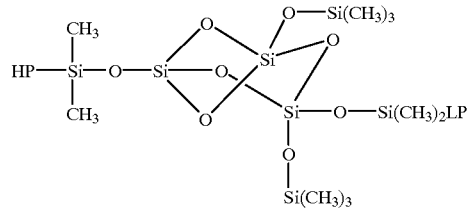

wherein LP is a lipophilic radical

HP is a hydrophilic radical
x is 0–5000
y is 0–5000, and
z is 0–5000, with the proviso that the organosiloxane contains at least on hydrophilic radical and at least one lipophilic radical.

More preferred are compounds of the generic formula I wherein LP is a lipophilic radical which is a $C_{1-40}$ straight or branched chain alkyl, HP is a hydrophilic radical containing hydroxy-polyethyleneoxy, and z is at least 1. Most preferred is a compound of the formula:

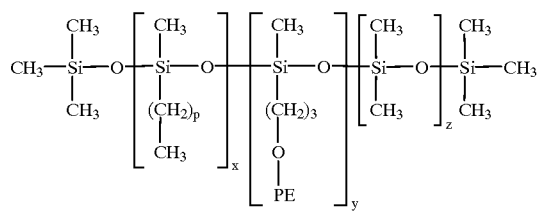

wherein p is 1–40, and

PE is $(-C_2H_4O)_a(-C_3H_6)_b-H$ where x, y, z, a, and b are such that the molecular weight of the polymer ranges from about 500 to 100,000. Organosiloxane polymers useful in the compositions of the invention are commercially available from Goldschmidt Corporation under the ABIL tradename. The preferred polymer is cetyl dimethicone copolyol and has the tradename ABIL WE 09 or ABIL WS 08.

Another type of preferred organosiloxane emulsifier suitable for use in the compositions of the invention are emulsifiers sold by Union Carbide under the Silwet™ trademark. These emulsifiers are represented by the following generic formulas:

$(Me_3Si)_{y-2}[(OSiMe_2)_{x/y}O-PE]_y$ wherein PE=$-(EO)_m(PO)_nR$

R=lower alkyl or hydrogen

Me=methyl

EO is polyethyleneoxy

PO is polypropyleneoxy m and n are each independently 1–5000 x and y are each independently 0–5000, and

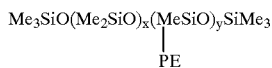

wherein PE=$-CH_2CH_2CH_2O(EO)_m(PO)_nZ$

Z=lower alkyl or hydrogen, and

Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

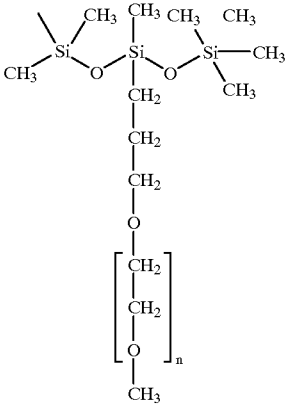

Wherein n is 1–10, preferably 8.

Another preferred organosiloxane emulsifier for use in the compositions of the invention is dimethicone copolyol. Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Amerchol under the Amersil tradename, including Arnersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2–5200, and the like are also suitable. In addition, surfactants sold under the tradename Silwet by Union Carbide, and surfactants sold by Troy Corporation under the Troysol tradename, hose sold by Taiwan Surfactant Co. under the tradename Ablusoft, those sold by Hoechst under the tradename Arkophob, are also suitable for use in the invention.

II. Gel Structure Modifiers

Preferably, the composition contains 1–50%, preferably 2–40%, more preferably 5–35% of at least on gel structure modifier. The term "gel structure modifier" means an ingredient which is capable of plasticizing the composition such that it exhibits improved pay off when applied to the skin. For example, antiperspirant stick or gel compositions, when applied to the skin, must deposit a certain amount of product onto the skin. The amount of material deposited onto the skin as the gel is rubbed across the skin surface is called "pay off". If a gel does not have adequate pay off, when the gel is rubbed across the underarm skin, a sufficient amount of the gel composition will not rub off onto the skin. On the other hand, if the gel has too much pay off, when it is rubbed across the underarm skin too much of the gel deposits on the skin. Thus, it is important to regulate the gel structure and consistency so that pay off is optimal. Generally, suitable gel structure modifiers include polyols, aliphatic short chain mono-, di, and polyhydric alcohols, ethoxylated and/or propoxylated fatty alcohols or glycols, monomer and polymeric ethers and block copolymers, and the like.

1. Polyols

Suitable polyols are defined as compounds which contain three or more hydroxyl groups per molecule. Examples of suitable polyols include fructose, glucamine, glucose, glucose glutamate, glucuronic acid, glycerin, 1,2,6-hexanetriol, hydroxystearyl methylglucamine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof.

2. Ethers

Also suitable as gel structure modifiers are homopolymeric or block copolymeric liquid others. Polymeric ethers are preferably formed by polymerization of monomeric alkylene oxides, generally ethylene or propylene oxides. Preferred monomeric ethers are those exhibiting the structure below were n=1. Preferred polymeric ethers are comprised of moieties having the general structure below wherein n=2 to 100:

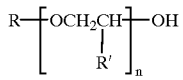

where R and R' are each independently H, or $C_{1-30}$ straight or branched chain alkyl, and n is 1 to 20. Examples of such polymeric ethers include PEG, PPG, PEG/PPG copolymers, and derivatives thereof as well as alkoxylated alcohols such as steareth 2–100, ceteth 2–100, and the like.

Other examples of suitable polymeric ethers include polyoxypropylene polyoxyethylene block copolymers having the general formula:

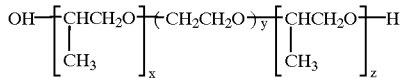

wherein x is 1–200, y is 1–200 and z is 1–200. Such compounds are sold under the CTFA name Meroxapol 105, 108, 171, 172, 174, 178, 251, 252, 254, 255, 258, 311, 312, and 314.

3. Alcohols

Mono- and dihydric alcohols are also suitable for use as gel structure modifiers. Generally, these mono- and dihydric alcohols have the general formula R(OH)n where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, methyl propanediol, and mixtures thereof 4. Sorbitan Derivatives Sorbitan derivatives, which are defined as ethers or esters of sorbitan, are also suitable gel structure modifiers. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

The invention will be further described in connection with the following examples which are set forth for the purposes of illustration only.

EXAMPLE 1

Antiperspirant stick compositions were prepared according to the following formulas:

|  | w/w % |
| --- | --- |
| Dimethicone copolyol | 2.00 |
| Cyclomethicone and dimethicone/vinyl dimethicone crosspolymer | 2.00 |
| Dipropylene glycol | 9.00 |
| 12-hydroxystearic acid | 5.00 |
| Al/Zr tetrachlorohydrex gly (43% aqueous sol.) | 58.00 |
| Acetamide MEA (70% sol.) | 1.00 |
| Agarose | 1.00 |
| Water | QS |

The compositions were made by mixing the agarose, dipropylene glycol, and water and heating the mixture to 100 to 105° C. with stirring until the composition was clear with no particulates remaining. The mixture was then cooled to 85 to 90° C. and the 12-hydroxystearic acid added. When all the material was completely melted and the mixture was uniform, then the temperature was reduced to 70 to 75° C. Separately, the cyclomethicone, dimethicone copolyol, and dimethicone/vinyl dimethicone crosspolymer were combined and mixed well and added to the cooled mixture. The acetamide MEA was then added to the mixture, which was then maintained at a temperature of 60 to 75° C. The aqueous antiperspirant salt solution was heated to a temperature of 50 to 65° C. and combined with the emulsion mixture with stirring. The resulting compositions were maintained at a temperature of 55 to 70° C. and poured into stick molds to provide opaque gel oil-in-water emulsions which hardened into solid sticks.

EXAMPLE 2

Antiperspirant stick compositions were prepared according to the following formulas:

|  | w/w % | |
| --- | --- | --- |
|  | (1) | (2) |
| Dimethicone copolyol | 2.00 | 4.00 |
| Cyclomethicone and dimethicone/vinyl dimethicone crosspolymer | 2.00 | 2.00 |
| Cyclomethicone | — | 30.00 |
| Dipropylene glycol | 9.00 | — |
| 12-hydroxystearic acid | 5.00 | — |
| Al/Zr tetrachlorohydrex gly (43% aqueous sol.) | 58.00 | 58.00 |
| Acetamide MEA (70% sol.) | 1.00 | 1.00 |
| Agarose | 1.00 | 1.00 |
| Water | QS | QS |

The compositions were made by mixing the agarose, dipropylene glycol, and water and heating the mixture to 100 to 105° C. with stirring until the composition was clear with no particulates remaining. The mixture was then cooled to 85 to 90° C. and the 12-hydroxystearic acid added. When all the material was completely melted and the mixture was uniform, then the temperature was reduced to 70 to 75° C. Separately, the cyclomethicone, dimethicone copolyol, and dimethicone/vinyl dimethicone crosspolymer were combined and mixed well and added to the cooled mixture. The acetamide MEA was then added to the mixture, which was then maintained at a temperature of 60 to 75° C. The aqueous antiperspirant salt solution was heated to a temperature of 50 to 65° C. and combined with the emulsion mixture with stirring. The resulting compositions were maintained at a temperature of 55 to 70° C. and poured into stick molds to provide opaque gel oil-in-water emulsions. Composition (1) provided an oil in water emulsion solid stick. Composition (2) provided a water in oil emulsion gel.

EXAMPLE 3

An emulsion antiperspirant stick composition was prepared according to the following formula:

|  | w/w % |
|---|---|
| Dimethicone copolyol | 2.0 |
| Emulsifying silicone elastomer* | 2.0 |
| Dipropylene glycol | 9.0 |
| 12-hydroxystearic acid | 5.0 |
| Al/Zr tetrachlorohydrex gly (43% aqueous solution) | 58.0 |
| Acetamide MEA (70% aqueous solution) | 1.0 |
| Agarose | 1.0 |
| Water | QS |

*KSG 21, a methylhydrogendimethylsiloxane cross linked with polyoxyalkylene.

The composition was made by mixing the agarose, dipropylene glycol, and water and heating the mixture to 100 to 105° C. with stirring until the composition was clear with no particulates remaining. The mixture was then cooled to 85 to 90° C. and the 12-hydroxystearic acid added. When all the material was completely melted and the mixture uniform, the temperature was reduced to 70 to 75 C. Separately, the dimethicone copolyol and the emulsifying siloxane elastomer were combined and mixed well and added to the cooled mixture. The acetamide MEA was then added to the mixture, which was then maintained at a temperature of 60 to 75° C. The aqueous antiperspirant salt solution was heated to a temperature of 50 to 65° C. and combined with the emulsion mixture with stirring. The resulting compositions were maintained at a temperature of 55 to 70° C. and poured into stick molds to provide opaque oil-in-water emulsions which hardened into solid sticks.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A water and oil emulsion solid antiperspirant composition comprising, by weight of the total composition:
   0.1–30% of a silicone elastomer,
   0.05–30% of a gellant,
   1–25% of an antiperspirant active,
   1–90% water, and
   1–75% oil.

2. The composition of claim 1 which is an oil in water emulsion.

3. The composition of claim 1 wherein the silicone elastomer is the reaction product of methyl hydrogen siloxane and a vinyl terminated organosiloxane.

4. The composition of claim 1 wherein the silicone elastomer is the reaction product of methyl hydrogen siloxane and an alpha omega diene.

5. The composition of claim 1 wherein the silicone elastomer is an emulsifying siloxane elastomer.

6. The composition of claim 1 wherein the gellant is selected from the group consisting of dibenzylidene alditols, a carboxylated salt gellant, a polysaccharide, a protein/polysaccharide complex, and mixtures thereof.

7. The composition of claim 1 wherein the gellant is a polysaccharide.

8. The composition of claim 1 wherein the oil is selected from the group consisting of a volatile oil, a nonvolatile oil, and mixtures thereof.

9. The composition of claim 8 wherein the volatile oil comprises cyclomethicone.

10. The composition of claim 8 wherein the nonvolatile oil comprises dimethicone.

11. The composition of claim 1 additionally comprising a nonionic silicone surfactant.

12. The composition of claim 11 wherein the nonionic silicone surfactant is dimethicone copolyol.

13. The composition of claim 1 additionally comprising a gel structure modifier.

14. A water and oil emulsion solid deodorant composition comprising, by weight of the total composition:
   0.1–30% of a silicone elastomer,
   0.05–30% of a gellant,
   1–20% of a deodorant active,
   1–90% water, and
   1–75% oil.

15. The composition of claim 14 wherein the silicone elastomer is the reaction product of methyl hydrogen siloxane and a vinyl terminated organosiloxane.

16. The composition of claim 14 wherein the silicone elastomer is the reaction product of methyl hydrogen siloxane and an alpha omega diene.

17. The composition of claim 14 wherein the silicone elastomer is an emulsifying silicone elastomer.

18. The composition of claim 14 wherein the deodorant active is selected from the group consisting of fragrances, ammonium phenolsulfonate, benzalkonium chloride, benzethonium chloride, bromochlorophene, cetylpyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarbone, triclosan, zinc phenolsulfonate, zinc ricinoleate, and mixtures thereof.

19. The composition of claim 14 wherein the oil is selected from the group consisting of a volatile oil, a nonvolatile oil, and mixtures thereof.

20. The composition of claim 14 wherein the composition additionally contains a nonionic silicone surfactant.

* * * * *